United States Patent
Kim et al.

(10) Patent No.: US 12,064,182 B2
(45) Date of Patent: Aug. 20, 2024

(54) CHART DISPLAY DEVICE FOR VISUAL ACUITY TESTS

(71) Applicant: HUVITZ CO., LTD., Anyang-si (KR)

(72) Inventors: Chang Sung Kim, Anyang-si (KR); Young Duk Seo, Anyang-si (KR)

(73) Assignee: HUVITZ CO., LTD., Anyang-si (KR)

( * ) Notice: Subject to any disclaimer, the term of this patent is extended or adjusted under 35 U.S.C. 154(b) by 507 days.

(21) Appl. No.: 17/533,298

(22) Filed: Nov. 23, 2021

(65) Prior Publication Data

US 2022/0183548 A1 Jun. 16, 2022

(30) Foreign Application Priority Data

Dec. 14, 2020 (KR) ........................ 10-2020-0174397

(51) Int. Cl.
*A61B 3/032* (2006.01)
*A61B 3/00* (2006.01)

(52) U.S. Cl.
CPC .............. *A61B 3/032* (2013.01); *A61B 3/005* (2013.01)

(58) Field of Classification Search
CPC ........ A61B 3/032; A61B 3/005; A61B 3/0075
USPC ................................ 351/200, 222, 239, 243
See application file for complete search history.

(56) References Cited

U.S. PATENT DOCUMENTS

| | | | |
|---|---|---|---|
| 9,211,061 B2 * | 12/2015 | Kasthurirangan ... | A61B 3/0025 |
| 10,016,128 B2 * | 7/2018 | Evans .................. | A61B 3/0025 |
| 2019/0015034 A1 * | 1/2019 | Bhandari ............. | A61B 5/4023 |

FOREIGN PATENT DOCUMENTS

| | | |
|---|---|---|
| JP | 06-83001 U | 3/1994 |
| JP | 10-314116 A | 12/1998 |
| KR | 10-2004-0080875 A | 9/2004 |

* cited by examiner

*Primary Examiner* — Tuyen Tra
(74) *Attorney, Agent, or Firm* — United One Law Group LLC; Kongsik Kim; Jhongwoo Peck

(57) ABSTRACT

A chart display device for a visual acuity test includes a chart display optical unit that emits a chart image generated by a chart display optical system to a front, and is rotatably coupled to a frame of the chart display device via a rotation shaft; a position indicator light source that indicates the height of an eye to be examined and emits a position identification light; a position detection sensor that detects the position identification light emitted from the position indicator light source, and thus detects the height of the eye to be examined; and a rotation driving unit that rotates the chart display optical unit around the rotation shaft, and thereby tilts an emission direction of the chart image so that the chart image emitted from the chart display optical unit is emitted in the direction of the eye to be examined.

5 Claims, 7 Drawing Sheets

CHART DISPLAY DEVICE FOR VISUAL ACUITY TESTS

CROSS-REFERENCE TO RELATED APPLICATION

This application claims priority to Korean Application No. 10-2020-0174397 filed on Dec. 14, 2020, which is incorporated herein by reference in its entirety.

TECHNICAL FIELD

The present invention relates to a chart display device for visual acuity tests, and more particularly, to a space-saving chart display device for visual acuity tests capable of tilting an optical system for projecting a chart for a visual acuity test according to the height of the eyes of an examinee.

RELATED ART

A chart display device is a device for presenting a chart (visual acuity chart) image used as a marker for measuring the visual acuity of an examinee to an eye to be examined. In general, a chart display device for visual acuity tests presents a chart image at a location of a predetermined distance, for example, 5 m away from an eye to be examined, and is used to measure the visual acuity by checking whether the examinee identifies the chart image.

On the other hand, there is also known a space-saving chart display device in which a chart display optical system consisting of a large number of optical elements is installed in a box-like housing for measuring visual acuity in a narrow space where a measurement distance of 5 m cannot be secured. FIG. 1 is a diagram showing an example of a common space-saving chart display device disclosed in Japanese Patent Application Laid-Open No. 10-314116. In the common chart display device shown in FIG. 1, the chart 2 is illuminated by the light source 1 to generate a predetermined chart image, and the generated chart image passes through the convex lens 3 and then is reflected by the reflection mirror 4 to be directed to the eye 6 to be examined. Since the chart 2 is located closer than the focal position of the convex lens 3, the virtual image 7 of the chart image formed at a location spaced a certain distance apart from the eye 6 to be examined is presented to the eye 6 to be examined. In such a space-saving chart display device, the chart image generated by the chart 2 illuminated by the light source 1 is sequentially reflected through the lens 3, mirror 4, and the like, and the chart image 7 is presented to the eye 6 to be examined while securing an optical path of, for example, 5 m. In FIG. 1, reference numeral 5 denotes the housing of the chart display device in which the chart display optical system is installed, and reference numeral 8 denotes the chart display unit installed at one end of the housing to pass the chart image therethrough.

In such a space-saving chart display device, when an examinee sits on a chair located in front of the chart display device for a visual acuity test, for example, it is necessary to adjust the tilting angle of the reflection mirror 4 so as to adjust the tilting angle of the optical axis AX of the chart image 7 irradiated to the eye 6 to be examined because the height of the eyes varies depending on the height of the examinee. In order to adjust this tilting angle, a control device in the form of a remote controller for tilting the reflection mirror 4 may further be provided, in addition to the operation panel (connected by wire or wirelessly) for selecting or adjusting the chart 2. In other words, the common chart display device comprises a chart display device body in which the chart display optical system is installed, an operation panel, and a tilting remote controller. However, this common space-saving chart display device has a drawback that not only a dedicated remote controller for tilting the optical system is separately required, but also the tilting angle of the optical system cannot be accurately controlled.

PRIOR ART LITERATURE (Patent Document 1) Japanese Patent Application Laid-Open No. 10-314116

SUMMARY

It is an object of the present invention to provide a chart display device for visual acuity tests capable of accurately controlling the tilting angle of an optical system according to the height of the eyes of an examinee.

It is another object of the present invention to provide a chart display device for visual acuity tests that does not have to use a dedicated remote controller for tilting an optical system.

In order to achieve the objects above, the present invention provides a chart display device for a visual acuity test, comprising: a chart display optical unit (20) that includes a chart display optical system capable of generating a chart image therein, emits the chart image generated by the chart display optical system to a front, is rotatably coupled to a frame (10) of the chart display device via a rotation shaft (12), and rotates by a predetermined angle in a forward and backward direction around the rotation shaft (12); a position indicator light source (60) that can be adjusted in height so as to indicate the height of an eye (6) to be examined and emits a position identification light; a position detection sensor (40) that is mounted on one end of the chart display device so as to face the eye (6) to be examined, detects the position identification light emitted from the position indicator light source (60), and thus detects the height of the eye (6) to be examined; and a rotation driving unit (50) that rotates the chart display optical unit (20) around the rotation shaft (12) according to the height of the eye (6) to be examined detected by the position detection sensor (40), and thereby tilts an emission direction of the chart image so that the chart image emitted from the chart display optical unit (20) is emitted in the direction of the eye (6) to be examined.

The chart display device for visual acuity tests in accordance with the present invention can accurately control the tilting angle of the optical system without using a dedicated remote controller for tilting the optical system.

DETAILED DESCRIPTION

Figure 1:
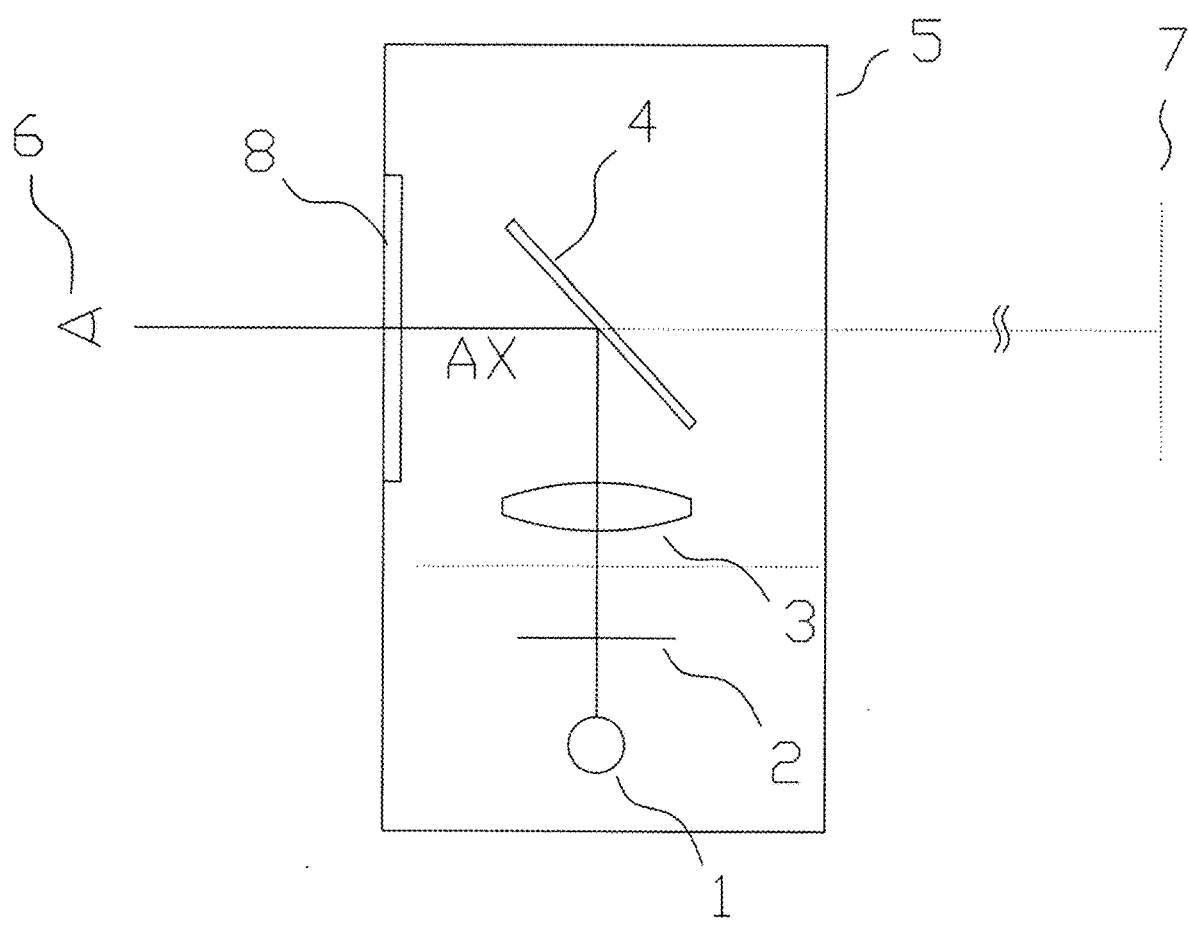
FIG. 1 is a diagram showing an example of a common space-saving chart display device.

Hereinafter, the present invention will be described in detail with reference to the accompanying drawings. In the accompanying drawings, elements performing the same or similar functions as in the prior art are assigned the same reference numerals.

Figure 2:
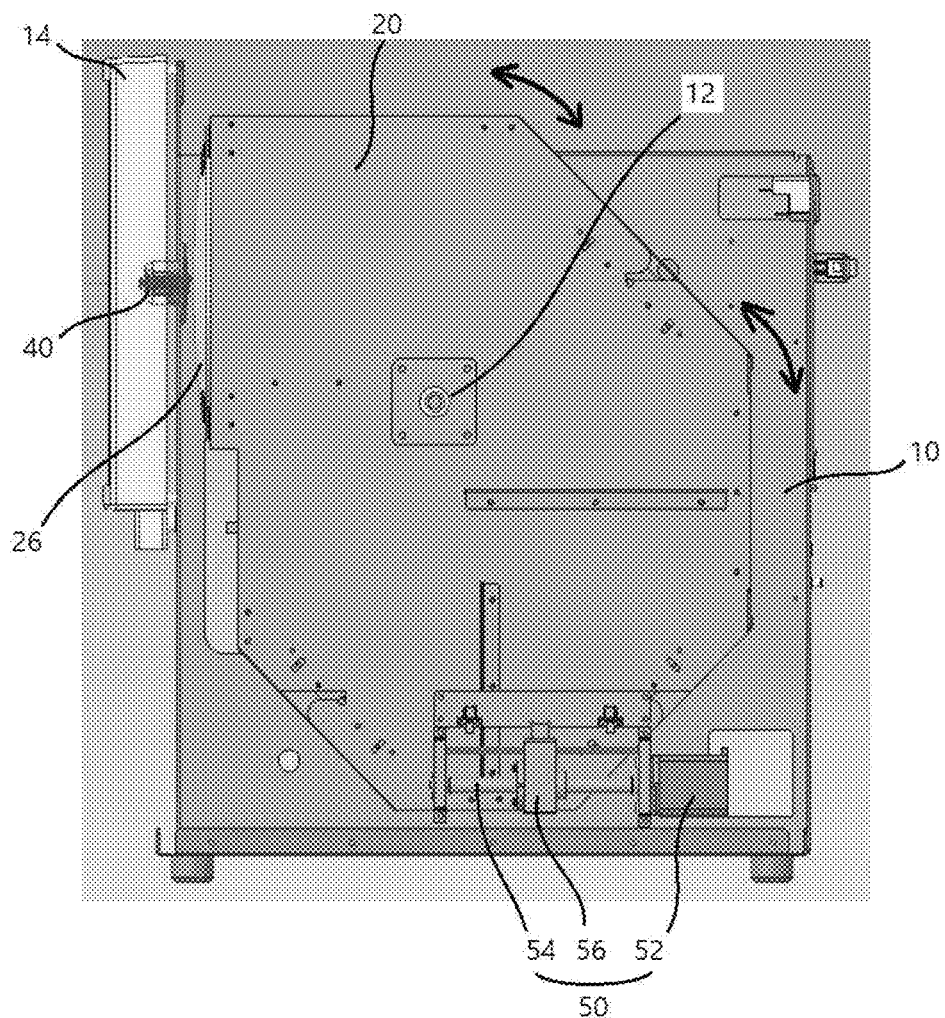
FIGS. 2 and 3 are a side view and a front view showing the internal configuration of a chart display device for visual acuity tests in accordance with one embodiment of the present invention.
Figure 3:
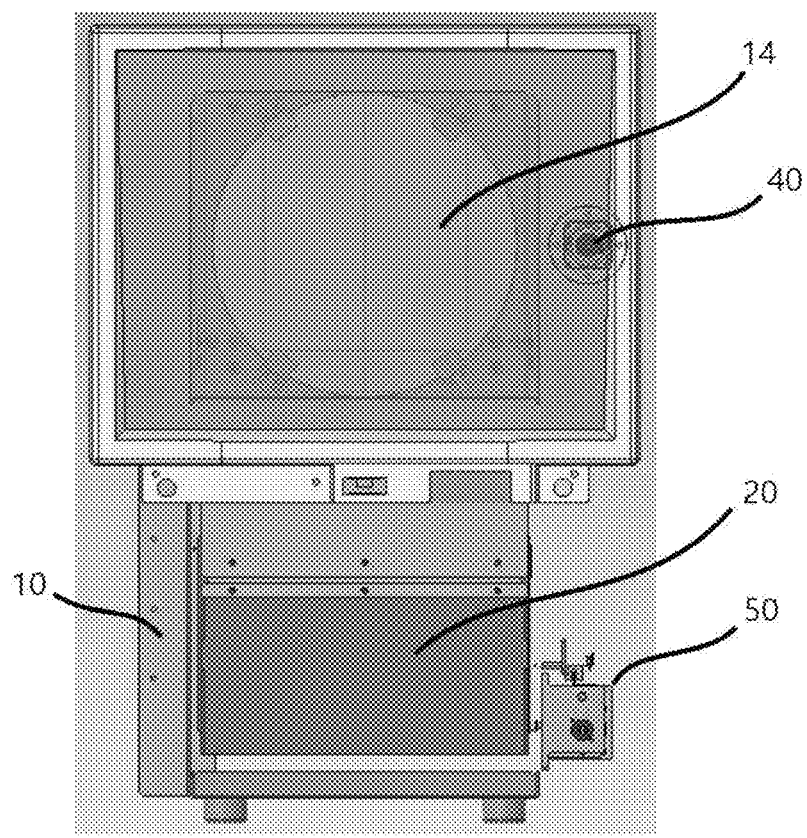
Figure 4:
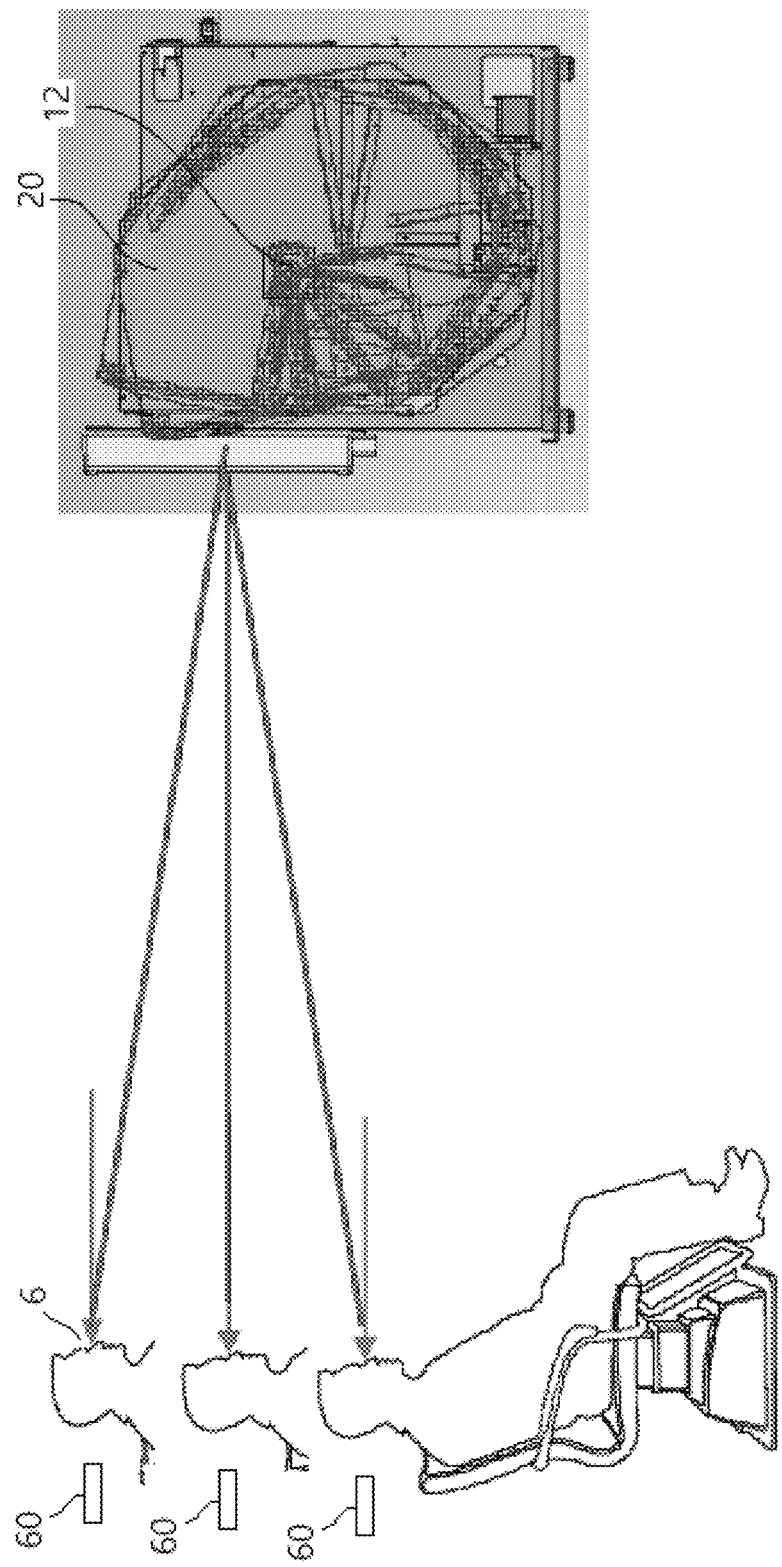
FIG. 4 is a diagram for illustrating the operation of a chart display device for visual acuity tests in accordance with one embodiment of the present invention.

FIGS. 2 and 3 are a side view and a front view showing the internal configuration of a chart display device for visual acuity tests in accordance with one embodiment of the present invention, and FIG. 4 is a diagram for illustrating the operation of a chart display device for visual acuity tests in accordance with one embodiment of the present invention. As shown in FIGS. 2 to 4, the chart display device for visual acuity tests in accordance with the present invention includes a chart display optical unit 20, a position indicator light source 60 (see FIG. 4), a position detection sensor 40, and a rotation driving unit 50. In FIGS. 2 and 3, reference numeral 10 denotes a frame of the chart display device, and reference numeral 14 denotes a chart display unit 14 such as a light-transmissive panel installed at one end of a housing of the chart display device for the chart image to pass therethrough. The chart display unit 14 also serves as a protective panel for protecting the chart display optical unit 20. In FIGS. 2 and 3, the housing of the chart display device is not shown.

Figure 5:
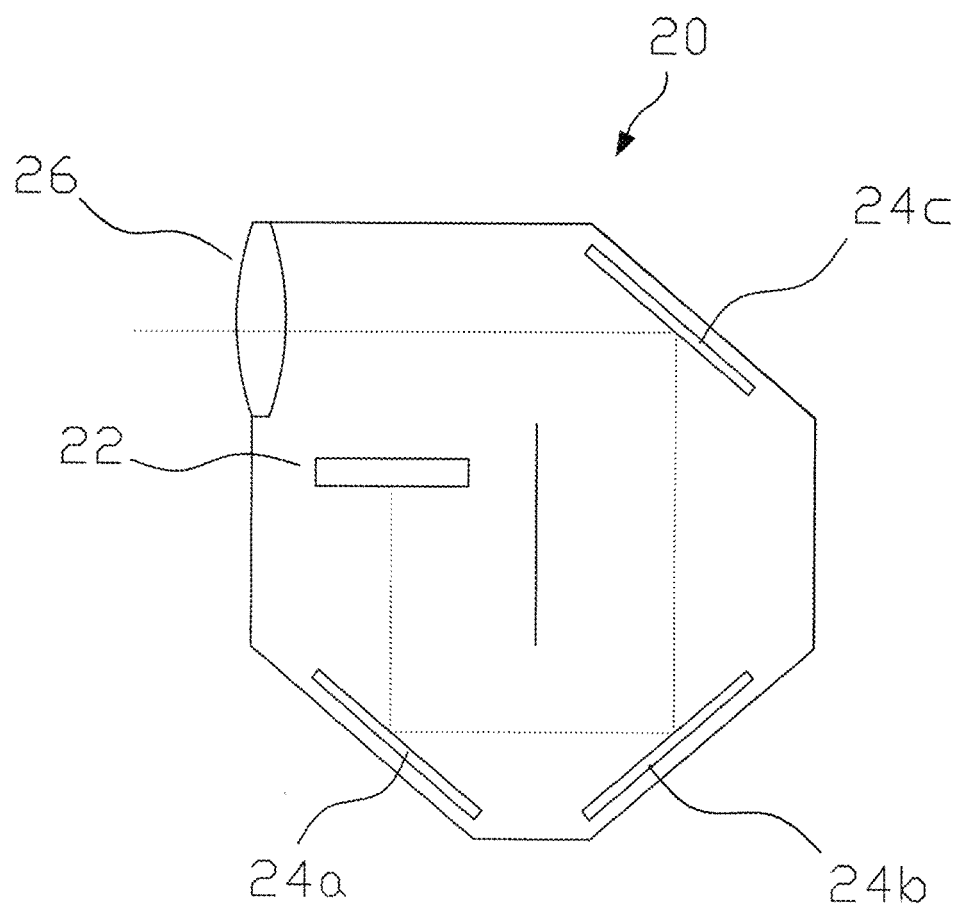
FIG. 5 is a diagram showing an example of a chart display optical system that may be included in a chart display optical unit used in the present invention.

The chart display optical unit 20 includes a chart display optical system capable of generating a chart image therein, emits the chart image generated by the chart display optical system to the front, is rotatably coupled to the frame 10 of the chart display device via a rotation shaft 12, and rotates by a predetermined angle in the forward and backward direction around the rotation shaft 12 (see arrows in FIG. 2). FIG. 5 is a diagram showing an example of a chart display optical system that may be included in the chart display optical unit 20 of the present invention. As shown in FIG. 5, the chart display optical system may include an image display device 22 for generating a chart image, one or more, for example, three reflection mirrors 24a, 24b, and 24c, which reflect and transmit the chart image emitted from the image display device 22, and a convex lens 26 for focusing the chart image. The image display device 22 is a common image generation device that generates a chart (optotype) image having a predetermined shape, for example, a shape such as , ○, Σ, and may be, for example, a small liquid crystal display device (LCD). The reflection mirrors 24a, 24b, and 24c serve to reduce the length of the chart display optical system by reflecting and changing the path of the chart image, and the convex lens 26 serves to form a virtual image of the chart image at a distance of 5 m with respect to the eye to be examined, by focusing the chart image, and thereby allowing the chart image at a first predetermined distance, for example, a distance of 1 m, to be formed as a virtual image at a second predetermined distance, for example, a distance of 4 m.

As shown in FIG. 4, the position indicator light source 60 can be adjusted in height so as to indicate the height of the eye 6 to be examined, and is a device for emitting a position identification light. The position indicator light source 60 may be a light source that emits infrared light, for example, infrared light having a wavelength of 940 nm as the position identification light. In the chart display device for visual acuity tests in accordance with the present invention, the chart display optical unit 20 may control chart changes, power on/off, etc., by a separate operation remote controller using infrared light, and the optotypes and menu functions displayed on the chart display optical unit 20 may be displayed on the operation remote controller. A common operation remote controller emitting infrared light as described above may also be used as the position indicator light source 60. As shown in FIG. 4, when an examinee sits in the examination position for a visual acuity test, the examiner positions the position indicator light source 60 at the height of the eye 6 to be examined of the examinee, and drives the position indicator light source 60 to emit a position identification light (e.g., infrared light).

Figure 6:
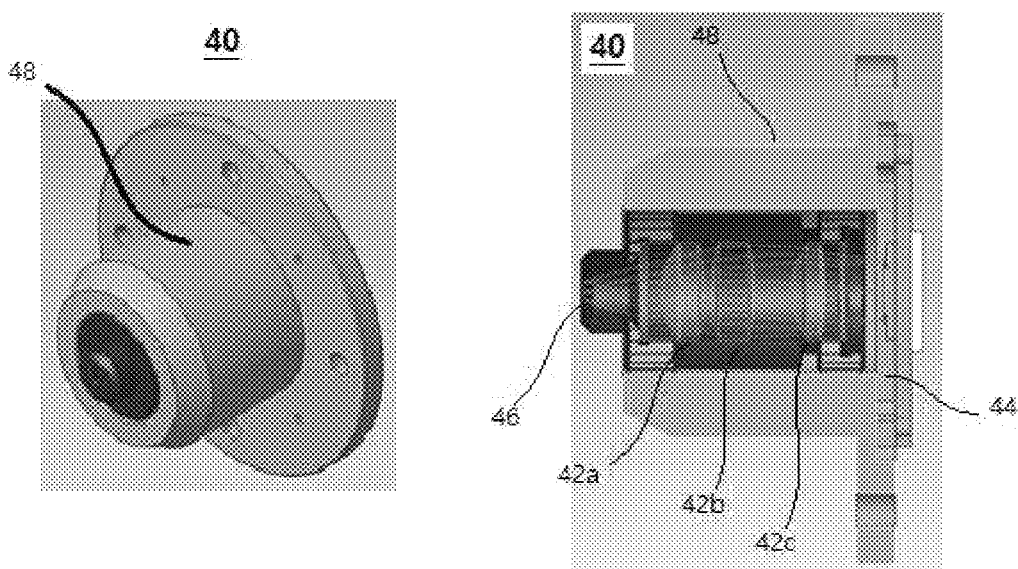
FIG. 6 is a perspective view and a side-sectional view of a position detection sensor that may be used in a chart display device in accordance with one embodiment of the present invention.
Figure 7:
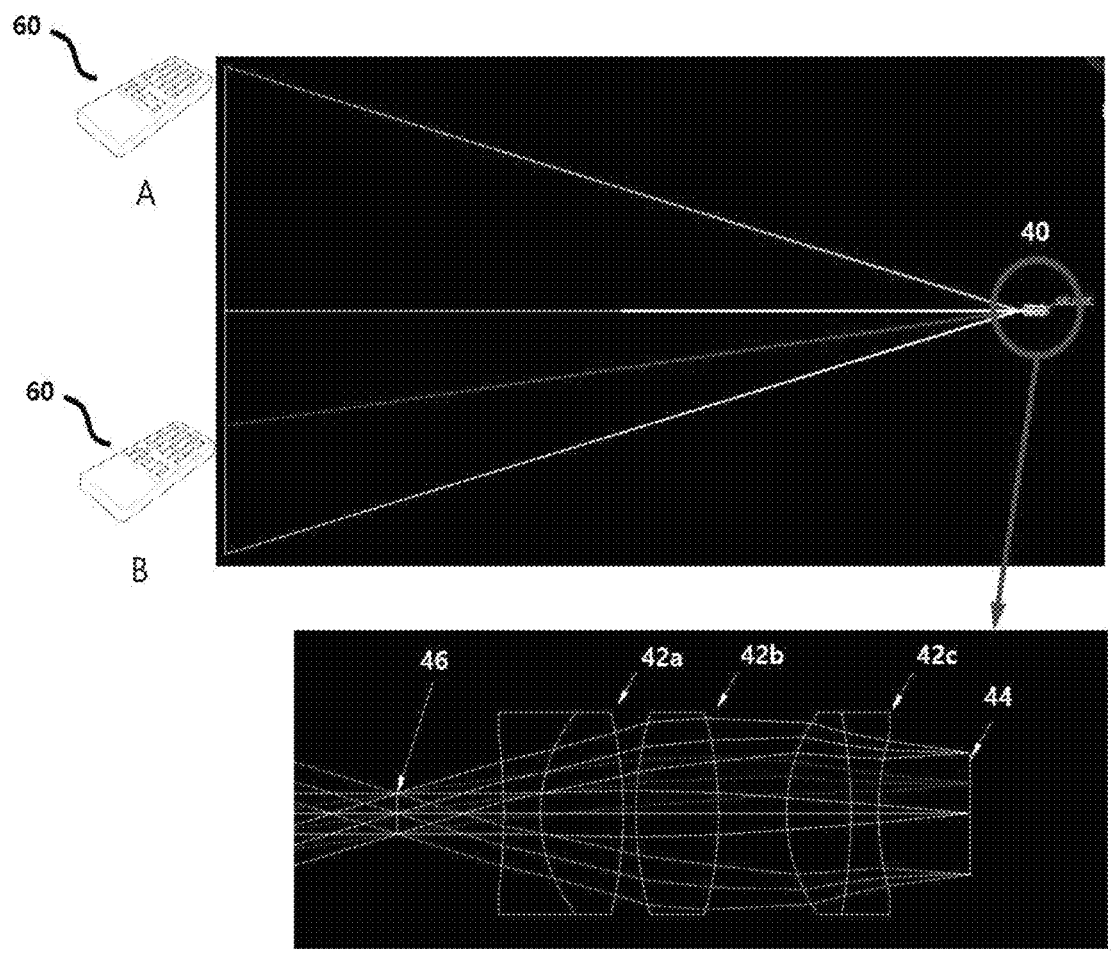
FIG. 7 is a diagram for illustrating a process of detecting the position of a position identification light and thereby detecting the height of the position indicator light source, in the position detection sensor that may be used in the present invention.

Referring again to FIGS. 2 and 3, the position detection sensor 40 is mounted on one end of the chart display device in accordance with the present invention so as to face the eye 6 to be examined, detects the position identification light emitted from the position indicator light source 60, and thus detects the height of the position indicator light source 60 with respect to the chart display device, i.e., the height of the eye 6 to be examined. As shown in FIGS. 2 and 3, the position detection sensor 40 may be installed at the same height as the chart display unit 14 that emits the chart image. FIG. 6 is a perspective view and a side-sectional view of a position detection sensor that may be used in a chart display device in accordance with one embodiment of the present invention. As shown in FIG. 6, the position detection sensor 40 has formed therein one or more focusing lenses 42a, 42b, and 42c for focusing the position identification light, a CMOS camera board 44 for detecting the position identification light focused by the focusing lenses 42a, 42b, and 42c, and a pin-hole 46 for allowing the position identification light to pass therethrough, and includes a sensor housing 48 that houses the focusing lenses 42a, 42b, and 42c and the CMOS camera board 44. FIG. 7 is a diagram for illustrating a process of detecting the position of a position identification light and thereby detecting the height of the position indicator light source 60, in the position detection sensor 40 that may be used in the present invention. As shown in FIG. 7, when the position indicator light source 60 such as an IR remote controller is positioned at the height of the eye 6 to be examined of an examinee seated for a visual acuity test (represented by A or B in FIG. 7), and the position identification light is emitted from the position indicator light source 60, the position identification light passes through the pin-hole 46 of the position detection sensor 40 and is focused by the one or more focusing lenses 42a, 42b, and 42c, and then the position identification light is detected at different locations of the CMOS camera board 44, depending on the emission location of the position identification light. Therefore, the position information of the eye 6 to be examined can be known according to the location where the position identification light is detected in the CMOS camera board 44. That is, the CMOS camera board 44 captures an image of the position identification light (infrared light), and detects the position of the eye 6 to be examined through image processing.

Referring again to FIGS. 2 to 4, the rotation driving unit 50 rotates the chart display optical unit 20 around the rotation shaft 12 according to the height of the eye 6 to be examined detected by the position detection sensor 40, and thereby tilts the emission direction of the chart image so that the chart image emitted from the chart display optical unit 20 is emitted in the direction of the eye 6 to be examined. The rotation driving unit 50 may be a common driving device capable of rotating the chart display optical unit 20. For example, as shown in FIGS. 2 to 3, the rotation driving unit 50 may include a drive motor 52 mounted on the frame 10 of the chart display device, a drive shaft 54 rotated by the drive motor 52, and a sliding unit 56 screw-coupled to the drive shaft 54 so as to be slidable along the drive shaft 54, and coupled to the chart display optical unit 20 to cause one end of the chart display optical unit 20 to slide in the forward and backward direction according to the rotation of the drive shaft 54. In this case, one end of the sliding unit 56 may be coupled, to be movable in the vertical direction, to a long hole (not shown) formed in the vertical direction at the chart display optical unit 20, so that the chart display optical unit 20 may be rotationally driven around the rotation shaft 12 when the sliding unit 56 moves forward and backward linearly (see FIGS. 2 and 4).

Next, a tilting operation of a chart display device for visual acuity tests in accordance with the present invention will be described. First, as shown in FIG. 4, when an examinee sits in the examination position for a visual acuity test, the position indicator light source 60, for example, the operation remote controller for controlling the chart display optical unit 20, is positioned next to the eye 6 to be examined of the examinee, and then the position indicator light source 60 is operated to cause a position indicator light (e.g., infrared light) to be generated at the height of the eye 6 to be examined. At this time, the position detection sensor 40 detects the height of the eye 6 to be examined from the location of the position indicator light detected on the CMOS camera board 44 (e.g., the red light in FIG. 7 detects location B, and the blue light detects location A). The control unit (not shown) of the chart display device drives the rotation driving unit 50 according to the detected height of the eye 6 to be examined, tilts the chart display optical unit 20, and emits a chart image in the direction of the eye 6 to be examined to match the height of the eye 6 to be examined. In other words, according to the present invention, the height of the eye 6 to be examined can be detected, by emitting a position identification light of the IR (940 nm) wavelength from next to the eye 6 to be examined of an examinee with a common remote controller and detecting the position identification light using the position detection sensor 40 including the CMOS camera board 44, and using this information, the chart display optical unit 20 can be tilted to match the height of the eye 6 to be examined.

According to the present invention, chart operation and optical system tilting are possible with one remote controller, by using a remote controller that emits infrared light (IR, e.g., infrared light having a wavelength of 940 nm) for wirelessly controlling (adjusting or selecting optotypes) the chart display optical unit 20 as the position indicator light source 60. Moreover, according to the present invention, since there is provided with a dedicated optical system for detecting the position of the eye 6 to be examined, the up and down/left and right positions of the eye 6 to be examined can be detected, the position of the eye 6 to be examined can be adjusted, or a chart image can be tilted and emitted in the direction of the eye 6 to be examined.

Although the present invention has been described above with reference to the accompanying drawings and exemplary embodiments, the present invention is not limited to what is shown in the drawings and the embodiments described above. Reference numerals are labeled in the following claims to aid understanding, but the scope of the following claims is not limited to the reference numerals and what is shown in the drawings, and should be construed to encompass all modifications, equivalent constructions and functions of the exemplary embodiments.

What is claimed is:

1. A chart display device for a visual acuity test, comprising:
   a chart display optical unit (20) that includes a chart display optical system capable of generating a chart image therein, emits the chart image generated by the chart display optical system to a front, is rotatably coupled to a frame (10) of the chart display device via a rotation shaft (12), and rotates by a predetermined angle in a forward and backward direction around the rotation shaft (12);
   a position indicator light source (60) that can be adjusted in height so as to indicate the height of an eye (6) to be examined and emits a position identification light;
   a position detection sensor (40) that is mounted on one end of the chart display device so as to face the eye (6) to be examined, detects the position identification light emitted from the position indicator light source (60), and thus detects the height of the eye (6) to be examined; and
   a rotation driving unit (50) that rotates the chart display optical unit (20) around the rotation shaft (12) according to the height of the eye (6) to be examined detected by the position detection sensor (40), and thereby tilts an emission direction of the chart image so that the chart image emitted from the chart display optical unit (20) is emitted in the direction of the eye (6) to be examined.

2. The chart display device for a visual acuity test of claim 1, wherein the chart display optical system comprises:
   an image display device (22) for generating a chart image;
   one or more reflection mirrors (24a, 24b, and 24c) that reflect and transmit the chart image emitted from the image display device (22); and
   a convex lens (26) for focusing the chart image.

3. The chart display device for a visual acuity test of claim 1, wherein the position indicator light source (60) is a light source that emits infrared light as the position identification light.

4. The chart display device for a visual acuity test of claim 1, wherein the position indicator light source (60) is an operation remote controller for controlling the chart display optical unit (20) by emitting infrared light.

5. The chart display device for a visual acuity test of claim 1, wherein the position detection sensor (40) has, formed therein, one or more focusing lenses (42a, 42b, and 42c) for focusing the position identification light, a CMOS camera board (44) for detecting the position identification light focused by the focusing lenses (42a, 42b, and 42c), and a pin-hole (46) for allowing the position identification light to pass therethrough, and comprises a sensor housing (48) that houses the focusing lenses (42a, 42b, and 42c) and the CMOS camera board (44).

\* \* \* \* \*